(12) United States Patent
Tang (10) Patent No.: US 9,017,301 B2
(45) Date of Patent: Apr. 28, 2015

(54) TRANSDERMAL DRUG DELIVERY SYSTEMS COMPRISING A COATED RELEASE LINER

(75) Inventor: Jiansheng Tang, South Burlington, VT (US)

(73) Assignee: Mylan Technologies, Inc., St. Albans, VT (US)

( * ) Notice: Subject to any disclaimer, the term of this patent is extended or adjusted under 35 U.S.C. 154(b) by 202 days.

(21) Appl. No.: 11/899,136

(22) Filed: Sep. 4, 2007

(65) Prior Publication Data

US 2009/0062754 A1  Mar. 5, 2009

(51) Int. Cl.
*A61F 13/02* (2006.01)
*A61M 37/00* (2006.01)
*A61K 9/70* (2006.01)

(52) U.S. Cl.
CPC ............. *A61M 37/00* (2013.01); *A61F 13/02* (2013.01); *A61K 9/703* (2013.01); *A61K 9/7053* (2013.01); *A61K 9/7092* (2013.01); *A61K 9/7084* (2013.01)

(58) Field of Classification Search
CPC ...... A61F 13/02; A61K 9/7084; A61M 37/00
See application file for complete search history.

(56) References Cited

U.S. PATENT DOCUMENTS

| | | | |
|---|---|---|---|
| 4,031,894 A | 6/1977 | Urquhart et al. | |
| 4,201,211 A | 5/1980 | Chandrasekaran et al. | |
| 4,559,222 A * | 12/1985 | Enscore et al. | 424/486 |
| 4,588,580 A | 5/1986 | Gale et al. | |
| 4,832,953 A | 5/1989 | Campbell et al. | |
| 4,839,174 A | 6/1989 | Baker et al. | |
| 4,882,377 A | 11/1989 | Sweet et al. | |
| 4,906,463 A | 3/1990 | Cleary et al. | |
| 4,908,213 A | 3/1990 | Govil et al. | |
| 4,915,950 A * | 4/1990 | Miranda et al. | 424/448 |
| 4,943,435 A | 7/1990 | Baker et al. | |
| 4,997,655 A | 3/1991 | Nagy et al. | |
| 5,006,342 A | 4/1991 | Cleary et al. | |
| 5,084,354 A * | 1/1992 | Krankkala et al. | 428/414 |
| 5,176,915 A | 1/1993 | Hoffmann | |
| 5,186,939 A | 2/1993 | Cleary et al. | |
| 5,198,476 A | 3/1993 | Kobayashi et al. | |
| 5,230,898 A | 7/1993 | Horstmann et al. | |
| 5,232,702 A | 8/1993 | Pfister et al. | |
| 5,543,231 A * | 8/1996 | Kidon et al. | 428/447 |
| 5,556,636 A | 9/1996 | Yano et al. | |
| 5,578,683 A | 11/1996 | Koch et al. | |
| 5,582,836 A | 12/1996 | Carli et al. | |
| 5,603,947 A | 2/1997 | Wong et al. | |
| 5,948,433 A * | 9/1999 | Burton et al. | 424/448 |
| 6,149,614 A * | 11/2000 | Dunshee et al. | 602/57 |
| 6,306,475 B1 | 10/2001 | Stocq et al. | |
| 6,337,086 B1 | 1/2002 | Kanios et al. | |
| 6,893,655 B2 | 5/2005 | Flanigan et al. | |
| 6,914,169 B1 | 7/2005 | Oota et al. | |
| 7,638,140 B2 | 12/2009 | Govil et al. | |
| 2002/0119187 A1 | 8/2002 | Cantor et al. | |
| 2003/0060479 A1 * | 3/2003 | Brown et al. | 514/282 |
| 2004/0028726 A1 * | 2/2004 | Fischer et al. | 424/449 |
| 2004/0202704 A1 | 10/2004 | Sharma et al. | |
| 2006/0078603 A1 | 4/2006 | Nguyen | |
| 2006/0127464 A1 | 6/2006 | Sugawara et al. | |
| 2007/0156076 A1 * | 7/2007 | Jackson et al. | 602/54 |
| 2009/0041832 A1 | 2/2009 | Govil et al. | |
| 2010/0040690 A1 | 2/2010 | Govil et al. | |

FOREIGN PATENT DOCUMENTS

| | | |
|---|---|---|
| JP | 59-206307 | 11/1984 |
| JP | 10036254 | 2/1998 |
| JP | 2000513608 A | 10/2000 |
| JP | 2002187836 A | 7/2002 |
| JP | 2002363069 A | 12/2002 |
| JP | 2003512414 A | 4/2003 |
| JP | 2004143052 A | 5/2004 |
| JP | 2005170865 A | 6/2005 |
| JP | 2005192619 A | 7/2005 |
| JP | 2007204437 A | 8/2007 |
| WO | 9800080 A1 | 1/1998 |
| WO | 0130316 A2 | 5/2001 |
| WO | 2005110482 A1 | 11/2005 |
| WO | 2008115371 A2 | 9/2008 |

OTHER PUBLICATIONS

Dailymed NIH(Sections: Catapres-TTS System Structure and Components and Cross Section of the System; Apr. 2006).*
International Search Report, PCT/US2008/10232.
Canadian Office Action for Application No. 2,698,495 dated Jun. 11, 2012.
Chinese Office Action for Application No. 200880114147.6 dated Apr. 19, 2012.
Australian Examination Report for Application No. 2008297001 dated Dec. 10, 2012.
Chinese Office Action for Application No. 200880114147.6 dated Mar. 18, 2013.
Extended European Search Report for Application No. EP 08795684 dated Aug. 6, 2013.
Arthur H Rogove: "Release Liners: A Review of Present Technology", Proceedings of the 1991 TAPPI Polymers, Laminations. and Coatings Conference, 1991, pp. 919-929.
European Search Report for Application No. EP08795684 dated Aug. 6, 2013.

(Continued)

*Primary Examiner* — Anoop Singh
*Assistant Examiner* — Anna Falkowitz (57) ABSTRACT

The present invention refers to a transdermal delivery device comprising a backing layer, at least one adhesive layer, and a release liner coated with a UV-cured highly crosslinked silicone. The present invention also refers to a method of preparing a transdermal delivery device comprising a backing layer, at least one adhesive layer, and a release liner coated with a UV-cured silicone.

10 Claims, 1 Drawing Sheet

(56) References Cited

OTHER PUBLICATIONS

Japanese Office Action for Application No. 2010523999 dated May 8, 2013.
Japanese office action for application No. 2010-523999 dated Nov. 8, 2013.
Mexican Office Action for Application No. MX/a2010/0/02452 dated Oct. 21, 2013.
Office Action from India for Application No. 1045/KOLNP/2010 dated Nov. 27, 2013.
Australian Examination Report for Application No. 2008297001 dated Jan. 16, 2014.
"Solutia's CPFilms Business Introduced New Optically Clear Polyester Protective Masking Film", Business Wire: A Bershire Hathaway Company, Apr. 20, 2005.

* cited by examiner

FIG. 3

TRANSDERMAL DRUG DELIVERY SYSTEMS COMPRISING A COATED RELEASE LINER

BACKGROUND OF THE INVENTION

The delivery of drugs through the skin provides many advantages. Primarily, it is a comfortable, convenient and noninvasive way of administering drugs. Moreover, such a means of delivery provides for uninterrupted therapy and a higher degree of control over drug concentrations in the blood.

In general, it is difficult to remove a thermally cured release liner from an adhesive layer or an intermediate laminate containing polyisobutylene ("PIB") and mineral oil without damaging the adhesive or intermediate layer. Usually, the greater the mineral oil to PIB ratio contained in the adhesive or intermediate layer, the more difficult it is to peel off the release liner. Because of this, special manufacturing processes are needed.

U.S. Pat. No. 4,201,211 discloses a transdermal delivery device comprised of a backing layer, a drug reservoir adhesive layer containing the drug clonidine, means for releasing clonidine from the reservoir, and means for affixing the patch to the skin. The patent teaches polyisobutene as an adhesive and mineral oil as a carrier for the clonidine.

U.S. Pat. No. 4,559,222 discloses a transdermal therapeutic system comprising a drug reservoir adhesive layer and an adhesive layer containing a moderately mineral oil soluble drug dispersed in the reservoir layer at a concentration above saturation. The patent also teaches a reservoir layer and an adhesive layer comprising a mixture of a mineral oil, polyisobutylene, and colloidal silicone dioxide. The patent further discloses a drug release rate controlling membrane disposed between the reservoir layer and the adhesive layer.

U.S. Pat. No. 4,832,953 discloses a scopolamine transdermal system comprising: a) a backing film; b) a drug reservoir adhesive layer comprised of polyisobutylene, mineral oil, and scopolamine base; c) a membrane layer; d) a skin contact adhesive layer comprised of polyisobutylene, mineral oil, and scopolamine base, and e) a siliconized release liner. The patent discloses a method of forming a device comprising the steps of a) casting a drug reservoir adhesive layer to a backing film to form an adhesive-backing layer laminate; b) casting a skin contact adhesive layer to a release liner to form an adhesive-release liner laminate; and c) laminating the adhesive-backing laminate and adhesive-release liner laminate to opposite sides of a membrane.

In each of U.S. Pat. Nos. 4,559,222 and 4,832,953, the drug reservoir adhesive layer is directly coated onto a backing layer. As a result, the backing film curves when the drug reservoir adhesive on backing film is dried, at an elevated temperature, in order to remove solvent.

U.S. Pat. No. 6,306,475 discloses a pressure-sensitive laminate and a method for making same, for which the release strength between an adhesive layer and a release liner can be selectively varied after the laminate has been manufactured by exposing the interface between the adhesive layer and the release liner to ultraviolet light. However, the prior art does not teach a UV-cured release liner which can be peeled off from a mineral oil containing transdermal system.

There remains the need for a release liner that can be easily peeled off from a mineral oil containing transdermal system without damage to the adhesive layer.

SUMMARY OF THE INVENTION

In accordance with the present invention applicants have invented a transdermal delivery device comprising a backing layer, at least one adhesive layer dispersed within said backing layer, and a release liner coated with a UV-cured highly crosslinked silicone. In accordance with one embodiment of the present invention, the release liner comprises a base film selected from the group consisting of polyethylene terephthalate, polypropylene, polyesters, and polyethylene. In accordance with another embodiment of the present invention, the base film comprises polyethylene terephthalate. In accordance with another embodiment of the present invention, the polyethylene terephthalate is from 0.5 mil to 5 mil thick. In accordance with another embodiment of the present invention, the UV-cured silicone coating ranges from about 2000 angstroms to about 10,000 angstroms thick.

In accordance with another embodiment of the present invention, the backing layer is selected from the group consisting of polyethylene films, polyethylene terephthalate films, nylon films, polypropylene films, polyester films, ethylene-vinyl acetate films, and metalized polyester films.

In accordance with another embodiment of the present invention, the at least one adhesive layer comprises an active pharmaceutical ingredient, and a mineral oil. In accordance with another embodiment of the present invention, the active pharmaceutical ingredient is selected from the group consisting of clonidine or scopolamine. In accordance with another embodiment of the present invention, the active pharmaceutical ingredient is present in an amount of about 1% to about 30% by weight of the at least one adhesive layer, preferably the active agent is present in an amount of about 2% to about 20% by weight of the at least one adhesive layer, most preferably the active agent is present in an amount of about 2% to about 15% by weight of the at least one adhesive layer.

In accordance with another embodiment of the present invention, the at least one adhesive layer comprises an adhesive selected from the group consisting of silicones, natural and synthetic rubbers, polyisobutylene, polyisobutylene blends, neoprenes, polybutadienes, polyisoprenes, polysiloxanes, acrylic adhesives, vinyl acetate adhesives, polyacrylates, ethylenevinylacetate copolymers, styrene-isoprene copolymers, polyurethanes, and mixtures thereof.

In accordance with another embodiment of the present invention, the amount of adhesive present in the at least one adhesive layer is about 34% to about 61.5% by weight of the adhesive layer, preferably about 38% to about 57% by weight of the adhesive layer, most preferably about 51% to about 55% by weight of the adhesive layer.

In accordance with another embodiment of the present invention, the at least one adhesive layer further comprises one or more additives. In accordance with another embodiment of the present invention, the one or more additives are selected from the group consisting of plasticizers, tackifiers, cohesion-promoting additives, stabilizers, colorants, dye, UV-absorbing compounds, antioxidants and fillers. In accordance with another embodiment of the present invention, the one or more additives are present in an amount of up to about 15% by weight of the at least one adhesive layer, preferably the one or more additives are present in an amount of about 1% to about 10% by weight of the at least one adhesive layer.

In accordance with another embodiment of the present invention, the at least one adhesive layer further comprises a cohesive promoting agent. In accordance with another embodiment of the present invention, the cohesive promoting agent is selected from the group consisting of colloidal silicone dioxides, zinc oxides, clays, bentonite, polyvinylpyrrolidines, acrylate copolymers, and crosspovidone. In accordance with another embodiment of the present invention, the cohesive promoting agent is present in an amount of up to about 15% by weight of the at least one adhesive layer, preferably the cohesive promoting agent is present in an amount of about 1% to about 15% by weight of the at least one adhesive layer.

In accordance with another embodiment of the present invention, the transdermal delivery device comprises one adhesive layer. In accordance with another embodiment of the present invention, the at least one adhesive layer comprises a first adhesive layer and a second adhesive layer, wherein each of the first and second adhesive layers contain the same or different amounts and/or types of active pharmaceutical ingredient, adhesive material, and/or mineral oil. In accordance with another embodiment of the present invention, the transdermal delivery device further comprises a membrane layer or non-woven layer between the first and second adhesive layers.

In accordance with another embodiment of the present invention, is a transdermal delivery device comprising a backing layer, a drug reservoir adhesive layer comprising an active pharmaceutical ingredient and a mineral oil, and a release liner coated with UV-cured silicone. In accordance with another embodiment of the present invention, the release liner comprises a base film selected from the group consisting of polyethylene terephthalate, polypropylene, polyesters, and polyethylene. In accordance with another embodiment of the present invention, the base film comprises polyethylene terephthalate. In accordance with another embodiment of the present invention, the polyethylene terephthalate is from about 0.5 to about 5 mil thick. In accordance with another embodiment of the present invention, the thickness of the UV-cured silicone coating ranges from about 2000 angstroms to about 10,000 angstroms.

In accordance with another embodiment of the present invention, the active pharmaceutical ingredient is selected from the group consisting of clonidine or scopolamine. In accordance with another embodiment of the present invention, the active pharmaceutical ingredient is present in an amount of about 1% to about 15% by weight of the drug reservoir adhesive layer, preferably the at least one active pharmaceutical ingredient is present in an amount of about 5% to about 10% by weight of the drug reservoir adhesive layer, most preferably the at least one active pharmaceutical ingredient is present in an amount of about 6% to about 9% by weight of the drug reservoir adhesive layer.

In accordance with another embodiment of the present invention, the drug reservoir adhesive layer comprises an adhesive selected from the group consisting of silicones, natural and synthetic rubbers, polyisobutylene, polyisobutylene blends, neoprenes, polybutadienes, polyisoprenes, polysiloxanes, acrylic adhesives, vinyl acetate adhesives, polyacrylates, ethylenevinylacetate copolymers, styrene-isoprene copolymers, polyurethanes, and mixtures thereof. In accordance with another embodiment of the present invention, the amount of adhesive ranges from about 34% to about 61.5% by weight of the drug adhesive layer, preferably the adhesive is present in an amount of about 35% to about 60% by weight of the adhesive layer, and most preferably the adhesive is present in an amount of about 38% to about 55% by weight of the adhesive layer.

In accordance with another embodiment of the present invention, the drug reservoir adhesive layer further comprises one or more additives. In accordance with another embodiment of the present invention, the one or more additives are present in an amount of up to about 40% by weight of the drug reservoir adhesive layer.

In accordance with another embodiment of the present invention, the drug reservoir adhesive layer further comprises a cohesive promoting agent. In accordance with another embodiment of the present invention, the cohesive promoting agent is selected from the group consisting of colloidal silicone dioxides, zinc oxides, clays, bentonite, polyvinylpyrrolidines, acrylate copolymers, and crosspovidone. In accordance with another embodiment of the present invention, the cohesive promoting agent is present in an amount of up to about 8% by weight of the drug reservoir adhesive layer.

In accordance with another embodiment of the present invention, the transdermal delivery device further comprises a skin contact adhesive layer between the drug reservoir adhesive layer and the release liner having none or at least one active pharmaceutical ingredient, a mineral oil, and an adhesive. In accordance with another embodiment of the present invention, the transdermal delivery device further comprises a membrane layer between the drug reservoir adhesive layer and the skin contact adhesive layer.

In accordance with the present invention is a transdermal delivery device comprising: a) a backing layer; b) a drug reservoir adhesive layer adjacent to the backing layer; c) a skin contact adhesive layer adjacent to the drug reservoir adhesive layer; and d) a release liner, adjacent to the skin contact adhesive layer, coated with UV-cured silicone.

In accordance with another embodiment of the present invention, the release liner comprises a base film selected from the group consisting of polyethylene terephthalate, polypropylene, polyesters, and polyethylene. In accordance with another embodiment of the present invention, the base film comprises polyethylene terephthalate. In accordance with another embodiment of the present invention, the polyethylene terephthalate is from about 0.5 to about 5 mil thick. In accordance with another embodiment of the present invention, the UV-cured silicone coating ranges from about 2000 angstroms to about 10,000 angstroms thick.

In accordance with another embodiment of the present invention, each of the drug reservoir and skin contact adhesive layers comprise an active pharmaceutical ingredient and a mineral oil. In accordance with another embodiment of the present invention, the active pharmaceutical ingredient is selected from the group consisting of clonidine and scolamine. In accordance with another embodiment of the present invention, the active pharmaceutical ingredient ranges from about 1% to about 30% by weight of the drug reservoir adhesive layer, and the active pharmaceutical ingredient ranges from about 0% to about 5% by weight of the skin contact adhesive layer.

In accordance with another embodiment of the present invention, the adhesive is selected from the group consisting of polyisobutylene and polyisobutylene blends. In accordance with another embodiment of the present invention, the adhesive ranges from about 34% to about 61.5% by weight of the drug reservoir and skin contact adhesive layers, preferably from about 35% to about 60% by weight of the adhesive layers.

In accordance with another embodiment of the present invention, the mineral oil ranges from about 20% to about 60% by weight of the drug reservoir and skin contact adhesive layers. In accordance with another embodiment of the present invention, each of said drug reservoir and skin contact adhesive layers further comprises one or more additives. In accordance with another embodiment of the present invention, each of said drug reservoir and skin contact adhesive layers further comprise a cohesive promoting agent. In accordance with another embodiment of the present invention, the cohesive promoting agent is colloidal silicone dioxide.

In accordance with another embodiment of the present invention, the transdermal delivery device further comprises a membrane or non-woven layer between the drug reservoir adhesive layer and the skin contact adhesive layer. In accordance with another embodiment of the present invention, the membrane or non-woven layer is a microporous membrane or a woven material.

In accordance with another embodiment of the present invention, a method of making a transdermal delivery device has been discovered comprising the steps of:
a) forming a wet adhesive blend comprising an active pharmaceutical ingredient, a mineral oil, an adhesive, and a solvent;
b) casting the wet adhesive blend to a release liner coated with UV-cured silicone;
c) drying the cast wet adhesive blend to form a dry adhesive;
d) laminating a backing film to the dry adhesive, and
e) die-cutting the laminate made in step d) to an appropriate size and shape.

In another embodiment of the present invention, the solvent is selected from the group consisting of heptane and ethyl acetate. In another embodiment of the present invention the active pharmaceutical ingredient is selected from the group consisting of clonidine and scopolamine. In another embodiment of the present invention, the adhesive is selected from the group consisting of polyisobutylene and polyisobutylene blends. In another embodiment of the present invention, the ratio of the mineral oil to the adhesive is from about 0.3:1.28 to about 0.5:0.9. In another embodiment of the present invention, the wet adhesive blend further comprises a cohesive promoting agent.

In accordance with the present invention the method of making a transdermal delivery device comprises the steps of:
a) forming a drug reservoir adhesive/backing layer laminate by:
  i) preparing a first wet adhesive blend,
  ii) casting the first wet adhesive blend to a first release liner coated with UV-cured silicone,
  iii) drying the cast first wet adhesive blend to form a drug release adhesive layer on the first release liner,
  iv) laminating a backing film to the drug release adhesive layer, and
  v) removing the first release liner from the drug release adhesive layer;
b) forming a skin contact adhesive/release liner laminate: by:
  i) preparing a second wet adhesive blend,
  ii) casting the second wet adhesive blend to a second release liner coated with UV-cured silicone, iii) drying the cast second wet adhesive blend to form a skin contact adhesive layer on the second release liner; and
c) laminating a top of the skin contact adhesive/release liner laminate to a top of the drug reservoir adhesive/backing layer laminate; and
d) die-cutting the laminate from step (c) to an appropriate size and shape.

In another embodiment of the present invention, the ratio of the mineral oil to the adhesive in the first wet adhesive blend is from about 0.4:1.65 to about 0.6 to 1.25. In another embodiment of the present invention, the ratio of the mineral oil to the adhesive in the second wet adhesive blend is from about 0.4:1.28 to about 0.6:0.9. In another embodiment of the present invention, the at least one of the first and second adhesive blends further comprises a cohesive promoting agent. In another embodiment of the present invention, the at least one of the first and second adhesive blends further comprises an additive selected from the group consisting of plasticizers, tackifiers, stabilizers, colorants, dyes, antioxidants, UV-absorbing compounds, and fillers. In another embodiment of the present invention further comprises the step of laminating a porous membrane or non-woven layer to an adhesive side of the drug adhesive/backing layer laminate. In another embodiment of the present invention the porous membrane or the non-woven film is pre-saturated with a mineral oil.

In accordance with the present invention the method of making a transdermal delivery device comprises the steps of:
a) forming a drug reservoir adhesive/backing layer laminate by:
  i) preparing a first wet adhesive blend,
  ii) casting the first wet adhesive blend to a first release liner coated with UV-cured silicone,
  iii) drying the cast first wet adhesive blend to form a drug release adhesive layer on the first release liner,
  iv) laminating a backing film to the drug release adhesive layer, and
  v) removing the first release liner from the drug release adhesive layer;
b) laminating a porous membrane or non-woven film, which may be pre-saturated with mineral oil, to the adhesive side of the drug reservoir/backing layer laminate;
c) forming a skin contact adhesive/release liner laminate: by:
  i) preparing a second wet adhesive blend,
  ii) casting the second wet adhesive blend to a second release liner coated with UV-cured silicone,
  iii) drying the cast second wet adhesive blend to form a skin contact adhesive layer on the second release liner;
d) laminating a top of the skin contact adhesive/release liner laminate to a top of the drug reservoir adhesive/backing layer laminate; and
e) die-cutting the laminate from step (d) to an appropriate size and shape.

In another embodiment of the present invention, the ratio of the mineral oil to the adhesive in the first wet adhesive blend is from about 0.4:1.65 to about 0.6 to 1.25. In another embodiment of the present invention, the ratio of the mineral oil to the adhesive in the second wet adhesive blend is from about 0.4:1.28 to about 0.6:0.9. In another embodiment of the present invention, the at least one of the first and second adhesive blends further comprises a cohesive promoting agent. In another embodiment of the present invention, the at least one of the first and second adhesive blends further comprises an additive selected from the group consisting of plasticizers, tackifiers, stabilizers, colorants, dyes, antioxidants, UV-absorbing compounds, and fillers. In another embodiment of the present invention further comprises the step of laminating a porous membrane or non-woven layer to an adhesive side of the drug adhesive/backing layer laminate. In another embodiment of the present invention the porous membrane or the non-woven film is pre-saturated with a mineral oil.

It has been unexpectedly discovered that a release liner coated with a UV-cured highly crosslinked silicone allows the release liner to be peeled from the adhesive layer containing the active pharmaceutical ingredient with only a small amount of force, even after the finished patch is stored at ambient or elevated temperatures for long periods of time. As a result of the ease of removal of the release liner, the adhesive layer remains intact and undamaged, allowing for complete and unhindered transdermal drug delivery. Moreover, the ease of removal allows for simplified methods of manufacturing multilayered transdermal devices without sacrificing the integrity of any layer of the device or requiring costly new manufacturing systems or processes.

DETAILED DESCRIPTION

The present invention is a transdermal delivery device comprising a backing layer, at least one adhesive layer, and a release liner coated with a UV-cured silicone. As used herein, "transdermal" means delivery of an active pharmaceutical ingredient into and through the skin or mucosal tissue. The figures depict transdermal delivery devices in the form of skin patches that, when applied to skin, function to transdermally deliver an active pharmaceutical ingredient.

Figure 1:
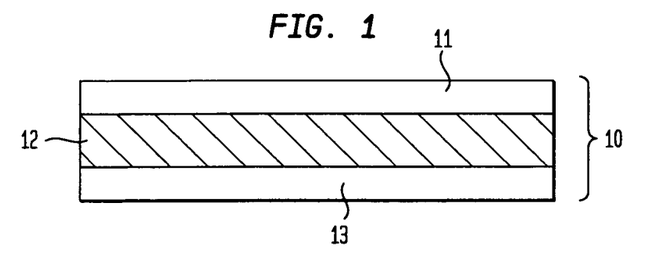
FIG. 1 is an enlarged, schematic, cross-sectional view of a 3-layered transdermal delivery device of the present invention.
Figure 2:
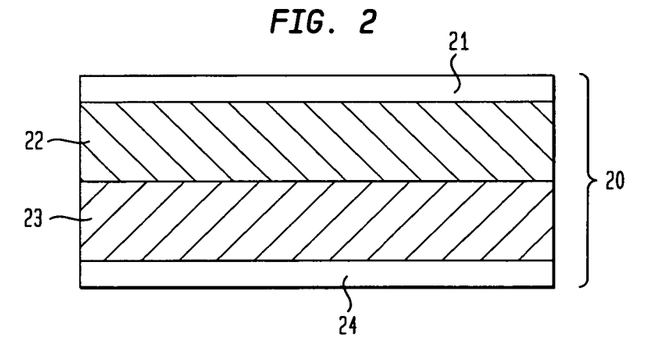
FIG. 2 is an enlarged, schematic, cross-sectional view of a 4-layered transdermal delivery device of the present invention.
Figure 3:
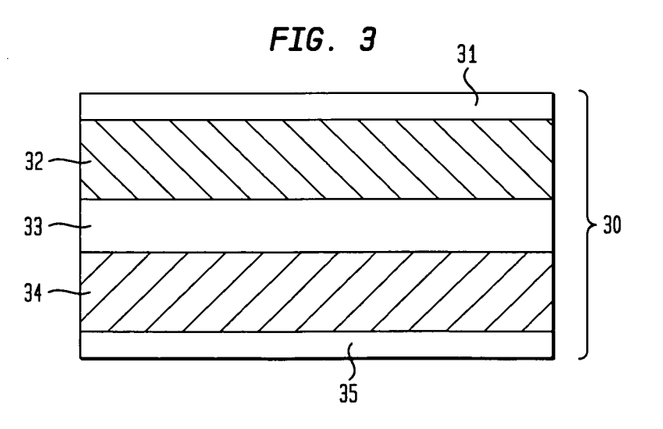
FIG. 3 is an enlarged, schematic, cross-sectional view of a 5-layered transdermal delivery device of the present invention.

In general, the transdermal delivery devices of the present invention are comprised of at least from three to five layers, depending on the number of adhesive layers included in the devices. FIG. 1 depicts a 3-layered transdermal delivery device 10 comprised of a backing layer 11, an adhesive layer 12, and a release liner coated with UV-cured highly crosslinked silicone 13. FIG. 2 depicts a 4-layered transdermal delivery device 20 comprised of a backing layer 21, two adhesive layers 22 and 23, and a release liner coated with UV-cured highly crosslinked silicone 24. FIG. 3 depicts a 5-layered transdermal delivery device 30 comprised of a backing layer 31, two adhesive layers 32 and 34, a membrane or non-woven layer 33 between the two adhesive layers, and a release liner coated with UV-cured highly crosslinkedsilicone 35. These figures merely represent embodiments of the invention. Those of skill in the art would appreciate that, for example, the adhesive layers represented may be of varying thicknesses.

The outermost layer of these transdermal delivery devices are the backing layers, 11, 21, or 31. The backing layer is a flexible substrate which provides a barrier against migration of an active pharmaceutical ingredient away from the intended direction of drug delivery and which provides support for the device. Any well-known backing layer which satisfies this purpose can be used in the present invention.

Non-limiting examples of materials from which the backing layer may be composed include polyethylene terephthalate, various nylons, polypropylenes, polyesters, polyester/ethylene-vinyl acetate, metalized polyester films, polyvinylidene chloride, metal films such as aluminum foils, polyvinylidene fluoride films, and mixtures, copolymers or laminates thereof. Specific backing layers which may be utilized include Mediflex® 1200, Mediflex® 1501, Mediflex® 1502, and Mediflex® 1503 (each available from Mylan Technologies, Inc.), and Scotchpak® 1109 (available from 3M). In a preferred embodiment, the backing layer is Mediflex® 1200.

Below and adjacent to the backing layer is the at least one adhesive layer. The at least one adhesive layer is comprised of an adhesive material, an active pharmaceutical ingredient, and a mineral oil. One type of adhesive layer is a drug reservoir adhesive layer. Another type of adhesive layer is a skin contact adhesive layer. While the drug reservoir adhesive layer and the skin contact adhesive layer may contain the same constituent components, the amounts and/or specific types of any one component may vary between the two layers depending on the desired structure of the system, the drug being delivered, and the release characteristics of the transdermal device.

In 3-layer transdermal delivery devices, only one adhesive layer, a drug reservoir adhesive layer 12, is present and located between a backing layer 11 and a release liner 13. In such embodiments, it is the drug reservoir adhesive layer 12 which contacts and adheres to the skin after the release liner 13 is removed (prior to application).

In 4-layer transdermal delivery devices, both a drug reservoir adhesive layer 22 and a skin contact adhesive layer 23 are present and adjacent to each other. The drug reservoir adhesive layer 22 is located below the backing layer 21 but above the skin contact adhesive layer 23, while the skin contact adhesive layer 23 is located below the drug reservoir adhesive layer 22 but above the release liner 24. In such embodiments, the skin contact adhesive layer 23 contacts and adheres to the skin after the release liner 24 is removed (prior to application).

In 5-layer transdermal delivery devices, both a drug reservoir adhesive layer 32 and a skin contact adhesive layer 34 are present, but separated by a membrane layer 33. The drug reservoir adhesive layer is located below the backing layer 31 but above the membrane layer 33, while the skin contact adhesive layer is located below the membrane layer 33 but above the release liner 35. In such embodiments, the skin contact adhesive layer 34 contacts and adheres to the skin after the release liner 35 is removed (prior to application).

The active pharmaceutical ingredient ("API") is dissolved within the adhesive matrix; partially dissolved and partially undissolved and dispersed within the adhesive matrix; dispersed (in a crystalline form) in the adhesive matrix; dispersed (in an amorphous form) in the adhesive matrix; or may be in an amorphous form partially dissolved and partially undissolved but dispersed in the adhesive matrix.

As used herein, the term "active pharmaceutical ingredient" is used to describe the principal active ingredient of the transdermal delivery device, which is a biologically active compound or mixture of compounds that has a therapeutic, prophylactic and/or physiological effect on the wearer of the device. The active pharmaceutical ingredient may be any active agent capable of being included within a transdermal delivery device.

Non-limiting examples of active pharmaceutical ingredients include anti-inflammatory substances, opioid receptor antagonists, anticholinergics, coronary dilators, cerebral dilators, peripheral vasodilators, alpha-adrenergic blockers, anti-infectives, psychotropics, anti-maniics, stimulants, anti-histamines, decongestants, gastro-intestinal sedatives, anti-anginal drugs, vasodilators, anti-arrhythmics, anti-hypertensive drugs, vasoconstrictors, migraine treatments, anti-coagulants and anti-thrombotic drugs, analgesics, anti-pyretics, hypnotics, sedatives, anti-emetics, anti-nauseants, anti-convulsants, neuromuscular drugs, hyper- and hypoglycemic agents, thyroid and anti-thyroid preparations, diuretics, anti-spasmodics, anti-emetic, uterine relaxants, anti-obesity drugs, anabolic drugs, erythropoietic drugs, anti-asthmatics, bronchodilators, expectorants, mucolytics, anti-uricemic drugs and the like.

In some embodiments of the present invention, the active pharmaceutical ingredient is clonidine. As used herein, the term "clonidine" is used to designate clonidine, the salts, solvates, and hydrates of clonidine, and the related compounds thereof.

In other embodiments of the present invention, the active pharmaceutical ingredient is scopolamine. As used herein, the term "scopolamine" is used to designate scopolamine, the salts, solvates, and hydrates of scopolamine, and the derivative compounds thereof (including, but not limited to, butylscopolamine).

In embodiments containing a single adhesive layer such as depicted in FIG. 1, the amount of active pharmaceutical ingredient present in the adhesive layer ranges from about 1% to about 25% by weight of the adhesive layer, preferably ranging from about 5% to about 20% by weight of the adhesive layer, and most preferably ranging from about 7% to about 9% by weight of the adhesive layer.

In embodiments containing two adhesive layers, such as depicted in FIGS. 2 and 3, the amount of active pharmaceutical ingredient in the drug reservoir adhesive layer ranges from about 1% to about 30% by weight of the drug reservoir adhesive layer, preferably from about 4% to about 20% by weight of the drug reservoir adhesive layer, most preferably from about 5% to about 15% by weight of the drug reservoir adhesive layer.

Similarly, in embodiments containing two adhesive layers such as depicted in FIGS. 2 and 3, the amount of active pharmaceutical ingredient in the skin contact adhesive layer ranges from about 0% to about 5% by weight of the skin contact adhesive layer, preferably from about 2% to about 4% by weight of the skin contact adhesive layer, most preferably from about 1% to about 2.5% by weight of the skin contact adhesive layer.

The "adhesive material" contained in the at least one adhesive layer may be any biocompatible polymer or polymeric material known in the art. The adhesive material may be selected from silicones, natural and synthetic rubbers, polyisobutylene ("PIB"), polybutenes, neoprenes, polybutadienes, polyisoprenes, polysiloxanes, acrylic adhesives including cross-linked and uncross-linked acrylic copolymers, vinyl acetate adhesives, polyacrylates, ethylenevinylacetate copolymers, styrene-isoprene copolymers, polyurethanes, plasticized weight polyether block amide copolymers, plasticized styrene-rubber block copolymers, and mixtures thereof. In embodiments containing more than one adhesive layer, the type of adhesive material chosen may be the same or different for each adhesive layer.

In one preferred embodiment, the adhesive material is polyisobutylene. In another preferred embodiment, a polyisobutylene blend is used comprising a low molecular weight PIB (about 25,000 to about 50,000 viscosity average molecular weight) and a high molecular weight PIB (about 700,000 to about 1,500,000 viscosity average molecular weight). In embodiments where a PIB blend is utilized, the ratio of low molecular weight PIB to high molecular weight PIB ranges from about 80:20 to about 60:40.

The amount of adhesive material present in the at least one adhesive layer ranges from about 34% to about 61.5% by weight of the adhesive layer, preferably ranging from about 38% to about 57% by weight of the adhesive layer, most preferably ranging from about 51% to about 55% by weight of the adhesive layer. In embodiments containing more than one adhesive layer, the amount of adhesive material may be the same or different for each adhesive layer.

Any mineral oil may be used provided it is compatible with the active pharmaceutical ingredient contained in the at least one adhesive layer. The mineral oil is an inert liquid that functions as a carrier for the active pharmaceutical ingredient. Generally, the mineral oil is a light mineral oil having a viscosity of about 7 cp at about 25° C.

The amount of mineral oil present in the at least one adhesive layer ranges from about 20% to about 60% by weight of the adhesive layer, preferably ranging from about 29% to about 50% by weight of the adhesive layer, most preferably ranging from about 32% to about 44% by weight of the adhesive layer. In embodiments containing more than one adhesive layer, the amounts of mineral oil may be the same or different for each adhesive layer.

In embodiments containing a single adhesive layer (FIG. 1), the ratio of mineral oil to adhesive ranges from about 0.3 to 1.28, preferably the ratio of mineral oil to adhesive ranges from about 0.4 to 1.0, and most preferably the ratio of mineral oil to adhesive ranges from about 0.5 to 0.9.

In embodiments containing two adhesive layers (such as depicted in FIG. 2 or 3), the ratios of mineral oil to adhesive are different for each of the adhesive layers. In a drug reservoir adhesive layer, the ratio of mineral oil to adhesive ranges from about 0.4 to 1.65, preferably the ratio of mineral oil to adhesive ranges from about 0.6 to 1.5, and most preferably the ratio of mineral oil to adhesive ranges from about 0.6 to 1.20. In a skin contact adhesive layer, the ratio of mineral oil to adhesive ranges from about 0.4 to 1.28, preferably the ratio of mineral oil to adhesive ranges from about 0.5 to 1.0, and most preferably the ratio of mineral oil to adhesive ranges from about 0.6 to 0.9.

The at least one adhesive layer may further comprise one or more cohesive promoting agents. The one or more cohesive promoting agents are selected from the group consisting of colloidal silicone dioxide, zinc oxide, polyvinylpyrrolidine, acrylate copolymers, crosspovidone, bentonites, clays, and mixtures thereof. In preferred embodiments, the cohesive promoting agent is colloidal silicon dioxide.

The amount of cohesive promoting agent present in the at least one adhesive layer ranges from about 0% to about 15% by weight of the adhesive layer, preferably ranging from about 3% to about 10% by weight of the adhesive layer, most preferably ranging from about 5% to about 8% by weight of the adhesive layer. In embodiments containing more than one adhesive layer, the amounts and/or types of cohesive promoting agent may be the same or different for each adhesive layer.

The at least one adhesive layer may further comprise one or more pharmaceutically acceptable additives. Non-limiting examples of additives include penetration enhancers, plasticizers, tackifiers, cohesion-promoting additives, stabilizers, fillers, colorants, dyes, UV-absorbing compounds, antioxidants and similar additives. The substances suitable for this purpose are known to those skilled in the art.

The amount of additives present in the at least one adhesive layer ranges from about 0% to about 40% by weight of the adhesive layer, preferably ranging from about 3% to about 20% by weight of the adhesive layer. In embodiments containing more than one adhesive layer, the amounts and/or types of additives may be the same or different for each adhesive layer.

Below and adjacent to the at least one adhesive layer is a release liner 13, 24, or 35. Prior to application and use of the transdermal delivery device, the release liner is peeled away from adhesive layer 12, 23, or 34 and discarded.

The release liner comprises a base film coated with silicone which is cured with ultraviolet light in the presence of a photoinitiator/catalyst. The base film may be selected from polymers including polyethyleneterephthalates ("PET"), polypropylenes, polyesters, and polyethylenes. The base film may be selected from about 0.5 mil to about 5 mil films of polyethyleneterephthalate, Toray F7S biaxially oriented polypropylene (BOPP), and high density polyethylene (HDPE), where 'mil' refers to the thickness of the base film coating and where 1 mil equals about $\frac{1}{1000}$ of an inch. In preferred embodiments, the base layer is about 1 mil to about 5 mil polyethyleneterephthalate, more preferably about 1 mil to about 3 mil PET.

A UV-cured highly crosslinked silicone coated release liner is manufactured according to the UV5A, UV10, UV12, UV30, UV50 methods, or according to the method associated with the Loparex Inc.'s UV-cured silicone coated release liner 2.0 CL PET 8000B(OUT)/000. The UV-cured silicon coating has a thickness ranging from about 1000 to about 10,000 angstroms, depending on the base film selected and the method of applying the silicon coating. In some embodiments, the UV-cured silicon coating has a thickness ranging from about 2000 to about 10,000 angstroms.

In preferred embodiments, the release-liner coated with a UV-cured silicon layer is selected from ClearSil®UV5A, Sil® Release Film UV5A, ClearSil®UV10, Sil® Release Film UV10, ClearSil®UV30, Sil® Release Film UV30, ClearSil®UV50, Sil® Release Film UV50, ClearSil®UV12, Sil® Release Film UV12, and ClearLES®UV12, all of which are available from CPFilms, Inc., Martinsville, Va. 24115).

The release liner coated with UV-cured silicone may be the same size as the at least one adhesive layer and/or may be the same size as the backing layer. In such instances, the release liner may range from about 0.1 mm to at least about 20 mm larger than the backing layer or the at least one adhesive layer (in each dimension), preferably ranging from about 0.5 mm to about 10 mm larger than the backing layer or the at least one adhesive layer, and most preferably ranging from about 1 mm to about 5 mm larger than the backing layer or the at least one adhesive layer.

In general, the release force necessary to remove a silicon coated release liner of the present invention ranges from about 5 to about 150 grams per inch, preferably from about 10 to about 90 grams per inch, even more preferably from about 10 to about 60 grams per inch.

In embodiments containing two adhesive layers, the transdermal delivery device may further comprise a membrane or non-woven layer 33. The membrane or non-woven layer 33 is located between the drug reservoir adhesive layer 32 and the skin contact adhesive layer 34. The membrane layer may serve a variety of purposes, such as controlling diffusion and providing controlled release of the active pharmaceutical ingredient(s). The membrane layer is selected such that it is rate controlling, i.e., the presence of the membrane layer in the device may change the skin penetration profile of the device compared to a like device not having the membrane. The non-woven layer may serve as an anchorage layer between the two adhesive layers.

Suitable membranes include continuous film membranes and microporous membranes. The membrane is preferably made of a flexible, polymeric material used conventionally by those skilled in the art. Polymer films which may be used for making the membrane layer include, without limitation, those comprising low density polyethylene, high density polyethylene, ethyl vinyl acetate copolymers, polypropylene and other suitable polymers. In one embodiment, the membrane layer is a microporous film membrane prepared from ethylene vinyl acetate copolymers containing from about 0.5 to about 28 wt. % vinyl acetate.

In a preferred embodiment, the membrane layer is a microporous polypropylene membrane, such as Celgard® 2400 (available from Celgard, LLCInc., Solupor 7-P-2.0 Cotran 9702, Cotran 9705, Cotran 9706, Cotran 9707, Cotran 9712 Cotran 9715, cotran 9716, Cotran 9728 (available from 3M™), and Solupor®10P05A (available fro DSM SoluTech).

The membrane thickness can generally range from about 10 mm to about 100 mm, preferably the thickness can range from about 15 mm to about 50 mm. In a preferred embodiment, the non-woven layer is comprised of a porous polyester fabric or rayon/polyester blends. One example of a non-woven layer is Sontara® from Dupont Nonwovens Sontara® Technologies. Their thickness may range from about 15 to about 30 mils with a corresponding unit weight of 0.7 to 2.4 oz/yard$^2$.

The present invention also relates to methods of manufacturing transdermal delivery devices comprising a backing layer, at least one adhesive layer, and a release liner coated with UV-cured silicon.

In one embodiment is a method of making a three-layered transdermal device 10 comprising a backing layer 11, a drug reservoir adhesive layer 12, and a release liner coated with a UV-cured silicone 13. First, a drug reservoir adhesive layer is prepared by casting a wet adhesive blend, which contains at least one active pharmaceutical ingredient, an adhesive, a mineral oil, and a solvent to a release liner coated with UV-cured silicone. The wet adhesive blend may also contain pharmaceutically acceptable additives and/or a penetration enhancer, as described herein. The solvent may be selected from any pharmaceutically acceptable solvent including, but not limited to, heptane and ethyl acetate. The cast wet adhesive blend is then dried in an oven to remove the solvent and form a dry adhesive. The dry adhesive is then laminated to a backing film to form the three-layered film. Individual devices (or patches) containing three layers are die-cut from the laminate.

In another embodiment is a method of making a four-layered transdermal device 20 comprising a backing layer 21, a drug reservoir adhesive layer 22, a skin contact adhesive layer 23, and a release liner coated with a UV-cured silicone 24. First, a drug reservoir adhesive layer on a backing film is prepared. A drug reservoir adhesive layer is prepared by casting a wet adhesive blend, which contains at least one active pharmaceutical ingredient, an adhesive, a mineral oil, and a solvent to a release liner coated with UV-cured silicone. The wet adhesive blend may contain pharmaceutically acceptable additives and/or cohesive promoting agents. The cast wet adhesive blend is then dried in an oven to remove the solvent and form a dry adhesive. The dry adhesive is then laminated to a backing film to form the three-layered film. The release liner is then peeled off leaving a drug reservoir on a backing film.

Second, a skin contact adhesive layer on a release liner is prepared. A skin contact adhesive layer is formed by casting a wet adhesive blend containing at least one active pharmaceutical ingredient, an adhesive, a mineral oil, and a solvent to a release liner coated with UV-cured silicone. The wet adhesive blend may also contain pharmaceutically acceptable additives and/or cohesive promoting agents. The solvent may be selected from any pharmaceutically acceptable solvent including, but not limited to, heptane and ethyl acetate. The cast wet adhesive blend is then dried in an oven to remove the solvent and form a dry adhesive.

Finally, to form the four-layer laminate, the top of the skin contact adhesive layer is laminated to the top of the drug reservoir adhesive layer. Individual devices (or patches) containing four layers are die-cut from the laminate.

In yet another embodiment is a method of making a five-layered transdermal device 30 comprising a backing layer 31, a drug reservoir adhesive layer 32, a skin contact adhesive layer 34, a membrane or non-woven layer 33, and a release liner coated with a UV-cured silicone 35. First, a drug reservoir adhesive layer on a backing film is prepared. A drug reservoir adhesive layer is prepared by casting a wet adhesive blend, which contains at least one active pharmaceutical ingredient, an adhesive, a mineral oil, and a solvent to a release liner coated with UV-cured silicone. The wet adhesive blend may contain pharmaceutically acceptable additives and/or cohesive promoting agents. The cast wet adhesive blend is then dried in an oven to remove the solvent and form a dry adhesive. The dry adhesive is then laminated to a backing film to form the three-layered film. The release liner is then peeled off leaving a drug reservoir on a backing film.

Second, a laminate having a membrane or non-woven layer, a skin contact adhesive layer, and a release liner is prepared. A skin contact adhesive layer is formed by casting a wet adhesive blend containing at least one active pharmaceutical ingredient, an adhesive, a mineral oil, and a solvent to a release liner coated with UV-cured silicone. The wet adhesive blend may contain pharmaceutically acceptable additives and/or cohesive promoting agents. The cast wet adhesive blend is then dried in an oven to remove the solvent and form a dry adhesive. A membrane or non-woven layer, as described previously, is laminated to the top of the adhesive layer. In some embodiments, the membrane layer is presaturated with mineral oil prior to lamination to the skin contact adhesive layer.

Finally, to form the five-layer laminate, the other side of the membrane or non-woven from the skin contact adhesive laminate is laminated to the top of the drug reservoir adhesive layer. Individual devices (or patches) containing five layers are die-cut from the laminate.

The following examples further illustrate the invention and its unique characteristics. These examples are not intended to limit the invention in any manner.

Examples 1 to 13

Patches or Intermediate Laminates Containing a Thermally Cured Silicone Release Liner A wet adhesive blend was prepared from light mineral oil, PIB (with a ratio of LMW/HMW of 55/45, the average LMW PIB is about 25000 to 35000 and the average HMW PIB is about 800,000 to 1,400,000 dalton) premix in heptane, CSD and clonidine base. The blend contains 32% solid by weight after removal of the volatile solvent. The blend was casted to a release liner as a thin film. The heptane is removed thermally. The adhesive film was laminated to a backing film Mediflex® 1200 to produce a laminate. A monolithic transdermal patch was made by die-cutting the laminate to an appropriate size and shape. The compositions of the resulting dry adhesive layer in the monolithic transdermal patch are described in table 1. An attempt was made to peel off the release liner from a patch or from an intermediate laminate. The results in table 1 indicate that no release liner could be peeled off or peeled off without completely or partially damaging the adhesive layer which has a weight ratio of mineral oil to PIB of 0.50 to 1.45, or 30 to 50% mineral oil by weight.

TABLE 1

| | Dry adhesive matrix composition | | | | | | Thermally | Was the release liner able to be peeled off or peeled |
|---|---|---|---|---|---|---|---|---|
| Ex. # | MO | PIB | MO/PIB ratio | CSD | Clon | Scop | Backing film | cured release liner | off without damaging the adhesive layer |
| 1 | 50.0 | 34.5[1] | 1.45 | 7.5 | 8 | 0 | Mediflex® 1200 | Medirelease® 2249, Scotchpak™ 1022 | No |
| 2 | 47.4 | 37.1[1] | 1.28 | 7.5 | 8 | 0 | Mediflex® 1200 | Medirelease® 2249, Scotchpak™ 1022 | No |
| 3 | 38.0 | 46.5[1] | 0.82 | 7.5 | 8 | 0 | Mediflex® 1200 | Medirelease® 2249 | No |
| 4 | 39.2 | 47.8[1-4] | 0.82 | 5.0 | 8 | 0 | Mediflex® 1200 | Medirelease® 2226 | No |
| 5 | 32.62 | 54.38[1,2,5-7] | 0.60 | 5.0 | 8 | 0 | Mediflex® 1200 | Medirelease® 2226 | No |
| 6 | 38.97 | 47.53[1] | 0.82 | 5 | 8.5 | | Mediflex® 1200 | Scotchpak™ 1022 | No |
| 7 | 33 | 55[1] | 0.60 | 5 | 7 | | Mediflex® 1200 | Scotchpak™ 1022 | No |
| 8 | 34 | 55[1] | 0.62 | 5 | 6 | | Mediflex® 1200 | Scotchpak™ 1022 | No |
| 9 | 47 | 32.5[2] | 1.45 | 7.5 | 13 | | Mediflex® 1200 | Scotchpak™ 1022 | No |
| 10 | 47 | 42.5[2] | 1.1 | 7.5 | 3 | | Mediflex® 1200 | Scotchpak™ 1022 | No |
| 11 | 41.60 | 50.90[1] | 0.82 | 7.5 | 0 | 0 | Mediflex® 1200 | Medirelease® 2226, Scotchpak™ 1022 | No |
| 12 | 49.91 | 41.59[1] | 1.20 | 8.5 | 0 | 0 | Mediflex® 1200 | Medirelease® 2226 Scotchpak™ 1022 | No |

TABLE 1-continued

| Ex. # | Dry adhesive matrix composition ||||| Backing film | Thermally cured release liner | Was the release liner able to be peeled off or peeled off without damaging the adhesive layer |
|---|---|---|---|---|---|---|---|---|
| | MO | PIB | MO/PIB ratio | CSD | Clon | Scop | | | |
| 13 | 49.09 | 40.91[1] | 1.20 | 10 | 0 | 0 | Mediflex® 1200 | Medirelease® 2226, Scotchpak™ 1022 | No |
| 14 | 30 | 60[1] | 0.50 | 10 | 0 | 0 | Mediflex® 1200 | Medirelease® 2249 | No |
| 15 | 42.8 | 52.2[1] | 0.82 | 5 | 0 | 0 | Mediflex® 1200 | Medirelease® 2226 | No |
| 16 | 35.63 | 59.37[1] | 0.60 | 5 | 0 | 0 | Mediflex® 1200 | Medirelease® 2226 | No |

[1]55% Vistanex LM-LC and 45% Vistanex MML-100.
[2]55% Oppanol B12 and 45% Vistanex MML-100.
[3]55% Oppanol B11 AND 45% mml-100.
[4]55% Oppanol B10% and 45% MML-100.
[5]55% Oppanol B11, 21.49 to 23.18% Oppanol B80 and 21.82 to 23.51% Oppanol 100.
[6]55% Oppanol B12 and 8.75 to 23.18 Oppanol B80% and 21.82 to 26.25% Oppanol B100.

Example 17 to 23

Peeling Off Release Liners from Aged Patches

Circular patches (10 cm$^2$) are prepared by die-cutting intermediate laminates comprising a backing film (Mediflex® 1200), an adhesive layer comprised of 39% mineral oil, 48% PIB 955% Vistanex LM-LC and 45% MML-100), 5% CSD, 8% clonidine base, and a thermally cured release liner (Scotchpak™ 1022, Scotchpa™9744, Medirelease® 2249, Medirelease® 2226), or a UV-cured release liner Sil®Release Liner UV5A) as described in table 2. The results in table 2 indicate that the peel force of a release liner from an adhesive layer was much higher when the release liner utilized was Medirelease® 2249, Medirelease® 2226, Scotchpak™1022 and Scotchpak™ 9744 than when the release liner utilized was Sil®Release Liner UV5A, which has a UV-cured silicone coating. The results indicate partial adhesive layer damage occurred when Medirelease® 2249, Medirelease® 2226, Scotchpak™1022 or Scotchpak™ 9744 were used as release liners. However, there was no adhesive damage when the Sil® Release Liner UV5A was peeled off from the patch.

Data also indicated that the release force increased for patches that were aged for 1 month at 25° C./60% RH or 40° C./75% RH when the release liner was Medirelease® 2249, Medirelease® 2226, Scotchpak™1022 or Scotchpak™ 9744. The release force, however, remained low when the Sil® UV5A release liner was utilized, even after the patches were aged for 1 month.

The results in table 3 further indicate that the release force of Scotchpak™ 1022 increased over a period of 6 months at 25° C. or at 40° C. However the release force of the Sil® Release Liner UV5A remained low for over a period of 6 months at 25° C. or at 40° C.

The peel force of the transdermal delivery devices of the present invention were measured with an Instron testing machine according to methods known to those of skill in the art.

TABLE 2

| | | | 1 months ||||
|---|---|---|---|---|---|---|
| | | Initial Ambient || 25° C./60% RH || 40° C./75% RH ||
| Example No. | Release liner* | Patch damage | Peel force, g/in | Patch damage | Peel force, g/in | Patch damage | Peel force, g/in |
| 17 | MR2249 | yes | 52 | yes | 79 | yes | 45 |
| 18 | MR2226 | yes | 110 | yes | 136 | yes | 143 |
| 19 | SC1022 | yes | 57 | yes | 42 | yes | 48 |
| 20 | SC9744 | yes | 70 | yes | 87 | yes | 93 |
| 21 | UV5A | yes | 12 | no | 15 | no | 15 |

*Release liner MR2249 is Medirelease ® 2249 and MR2226 is Medirelease ® 2226, both are manufactured by Mylan Technologies Inc. SC1022 and SC9744 are Scotchpak ™ 1022 and Scotchpak ™ 9744, both are manufactured by 3 M. UV5A is Sil ® Release Liner UV5A, manufactured by CPFilms Inc.

TABLE 3

| | | | 1 month Peel force, g/inch || 2 months | 3 months Peel force, g/inch || 6 months peel force, g/inch ||
|---|---|---|---|---|---|---|---|---|---|
| Example No. | Release liner* | Initial | 25° C. 60% RH | 40° C. 75% RH | 40° C. 75% RH | 25° C. 60% RH | 40° C. 75% RH | 25° C. 60% RH | 40° C. 75% RH |
| 22 | SC1022 | 86 | 73 | 85 | 85 | 68 | 102 | 74 | 115 |
| 23 | UV5A | 12 | 15 | 15 | 17 | 13 | 19 | 16 | 17 |

*SC1022 is Scotchpak ™ 1022, manufactured by 3 M. UV5A is Sil ® Release Liner UV5A, manufactured by CPFilms Inc.

Example 24

Manufacturing of a Transdermal System Containing Two Adhesive Layers and a Membrane Layer

In this example, a drug reservoir adhesive layer was formed by casting a wet adhesive blend, which contains clonidine base, mineral oil, PIB, colloidal silicon dioxide and heptane (the wet blend has 32% solid by weight) to Sil® Release Liner UV5A film and drying the adhesive film in an oven. The dry adhesive film contains 13% clonidine, 47% mineral oil, 32.5% PIB (55% Oppanol B12 and 45% Vistanex MML-100) and 7.5% colloidal silicon dioxide by weight. The top of adhesive layer was laminated to a backing film Mediflex®1200 polyester side. The UV-cured release liner was easily peeled off without damaging the adhesive layer. This is the drug reservoir adhesive layer on backing film. A skin contact adhesive layer was formed by casting a wet adhesive blend containing clonidine, mineral oil, PIB, colloidal silicon dioxide and heptane to a Sil® Release Liner UV5A film and by drying the adhesive film in an oven. The dry adhesive film contains 3% clonidine, 47% mineral oil, 42.5% PIB and 7.5% colloidal silicon dioxide by weight. A Celguard® 2400 porous membrane, which was pre-saturated with mineral oil, was laminated to top of the skin contact adhesive layer. This is the three-layer skin contact adhesive laminate. To form a five-layer laminate, the other side of the membrane from the skin contact adhesive laminate was laminated to top of the drug reservoir adhesive layer. Patches were die-cut from the five-layer intermediate laminate. The UV-cured release liner (Sil® Release Liner UV5A) was able to be easily peeled off from the skin contact adhesive layer.

Example 25

Manufacturing of a Transferal System Containing Two Adhesive Layers and a Membrane Layer

The five-layer transdermal system in example 22 was manufactured in the same way as in example 21 except the Celguard® 2400 membrane was not pre-saturated with mineral oil. The drug reservoir adhesive layer contains 51.64% mineral oil, 29.65% PIB (55% Oppanol B12 and 45% Vistanex MML-100), 6.8% colloidal silicon dioxide and 11.86% clonidine. The skin contact adhesive layer contains 51.64% mineral oil, 38.78% PIB (55% Oppanol B12 and 45% Vistanex MML-100), 6.84% colloidal silicon dioxide and 2.74% clonidine. The UV-cured Sil® Release Liner UV5A was able to be easily peeled off from the drug reservoir adhesive layer and from the skin contact adhesive layer.

Example 26

Manufacturing of a Transdermal System Containing Two Adhesive Layers and No Membrane Layer

In this example, a drug reservoir adhesive layer was formed by casting a wet adhesive blend, which contained clonidine base, mineral oil, PIB (55% Oppanol B12, 20.39% Oppanol B80 and 24.61% Oppanol B100), colloidal silicon dioxide and heptane (the wet blend had 32% solid by weight) to UV-cured Sil® Release Liner UV5A film and drying the adhesive film in an oven. The dry adhesive film contains 13% clonidine, 47% mineral oil, 32.5% PIB and 7.5% colloidal silicon dioxide by weight. The top of adhesive layer was laminated to a backing film Mediflex®1200 polyester side. The UV-cured release liner was easily peeled off without damaging the adhesive layer. This is the drug reservoir adhesive layer on backing film. A skin contact adhesive layer was formed by casting a wet adhesive blend containing clonidine, mineral oil, PIB, colloidal silicon dioxide and heptane to a Sil® Release Liner UV5A film and by drying the adhesive film in an oven. The dry adhesive film contains 3% clonidine, 47% mineral oil, 42.5% PIB and 7.5% colloidal silicon dioxide by weight. To form a four-layer laminate, the top of the skin contact adhesive layer was laminated to top of the drug reservoir adhesive layer. Patches were die-cut from four-layer intermediate laminate. The UV-cured release liner (Sil® Release Liner UV5A) was able to be easily peeled off from the skin contact adhesive layer.

Example 27

Manufacturing of a Transdermal System Containing Two Adhesive Layers and No Membrane Layer

Example 27 is the same as example 26 except the release liner in example 27 was Clear® Release Liner UV10. The UV-cured release liner (Clear® Release Liner UV10) in example 27 was able to be easily peeled off without causing any damage to the adhesive layer.

Example 28

Manufacturing of a Transdermal System Containing Two Adhesive Layers and No Membrane Layer

Example 28 is the same as example 26 except the release liner in example 28 was UV-cured Clear® Release Liner UV50. The UV-cured release liner (Clear® Release Liner UV50) in example 28 was able to be easily peeled off without causing any damage to adhesive layer.

Example 28

Manufacturing of a Transdermal System Containing Two Adhesive Layers and No Membrane Layer

Example 29 is the same as example 26 except the release liner in example 29 was a UV-cured silicone release liner 2.0 CL PET 8000B(out)/000 available from Loparex Inc. The release liner (Clear® Release Liner UV50) in example 29 was able to be easily peeled off without causing any damage to adhesive layer.

Example 30

Manufacturing of a Transdermal System Containing a Single Adhesive Layer Containing Scopolamine Base

A single adhesive layer laminate was prepared by casting a wet adhesive blend, which contained scopolamine, polybutylene (55% Oppanol B12 and 45% Oppanol 100 in heptane) and mineral oil, to Sil®Release Liner UV5A, heptane and ethyl acetate (the wet adhesive had 23% solid). After the adhesive film was dried in an oven, it was laminated to a backing film Mediflex® 1502. The dry adhesive contained 10% scopolamine base, 57% PIB and 33% mineral oil. Patches were die-cut from the laminate. The UV-cured release liner (Sil® Release Liner UV5A) was able to be easily peeled off from the patches without damaging the adhesive film.

Example 31

The patch in this example was the same as the patch in example 30 except the backing layer was Mediflex 1200. The UV-cured release liner (Sil® Release Liner UV5A) was able to be easily peeled off without damaging the adhesive film.

Example 32

The patch in this example was the same as the patch in example 30 except the backing was Mediflex 1000. The UV-cured release liner (Sil® Release Liner UV5A) was able to be easily peeled off without damaging the adhesive film

TABLE 4

Release liners coated with UV cured silicone available from CPFilms, Inc.

| | Works best | Will work | Intermediate range | Preferred range | Example of best UA cured silicone release liners |
|---|---|---|---|---|---|
| Base film | 2 mil and 3 mil Dupont Mylar A PET, 2 mil and 3 mil SKC SG-00 PET | Toray F7S, Biaxially oriented polypropylene (BOPP), HDPE, 2 mil and 3 mil Dupont Mylar A PET, 2 mil and 3 mil SKC SG-00 PET | Toray F7S, Biaxially oriented polypropylene (BOPP), HDPE, 2 mil and 3 mil Dupont Mylar A PET, 2 mil and 3 mil SKC SG-00 PET | Toray F7S, Biaxially oriented polypropylene (BOPP), HDPE, 2 mil and 3 mil Dupont Mylar A PET, 2 mil and 3 mil SKC SG-00 PET | 1) Sil ™ UV5A silicone release liner CPFilms Inc. product # 63U41002; 2) ClearSil ™ UV5A silicone release liner, CPFilms Inc. product # 6343002 |
| Polysiloxane coating | One side and two sided coated | One side and two sided coated | One side and two sided coated | One side and two sided coated | One side coated |
| Polysiloxane curing method | UV5A | UV5A, UV10, UV12 | UV5A, UV10, UV12 | UV5A | UV5A |
| Polysiloxane coating thickness | 4000 to 6000 Angstroms | 2000 to 10000 angstroms | 3000 to 7000 angstroms | 3000-7000 angstroms | 4000 to 6000 angstroms |
| 3M 610 release force | 5-21 | 2-100 | 2-60 | 2-40 | 7.7 g/inch |
| Release force from clonidine adhesive | 10-30 | 5-150 | 10-90 | 10-60 | 16 |
| Product name | ClearSil ® Clear Film UV5A Sil ® Release film UV5A | ClearSil ® Clear Film UV5A, UV 10, UV 12; Sil ® Release Film UV5A, UV10, UV12; ClearLES ® UV12 | ClearSil ® Clear Film UV5A, UV 10, UV 12; Sil ® Release Film UV5A, UV10, UV12; ClearLES ® UV12 | ClearSil ® Clear Film UV5A, UV 10, UV 12; Sil ® Release Film UV5A, UV10, UV12; ClearLES ® UV12 | ClearSil ® Clear Film UV5A, Sil ® Release film UV5A, ClearLES ® UV12 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A transdermal delivery device comprising a backing layer, an adhesive layer, and a release liner coated with UV-cured silicone, wherein said adhesive layer comprises 39 weight percent (wt %) of a mineral oil, 48 wt % of polyisobutylene (PIB), 8 wt % of an active pharmaceutical ingredient, and 5 wt % of colloidal silicon dioxide (CSD), wherein said PIB of said adhesive layer is in contact with the release liner, and wherein said active pharmaceutical ingredient is clonidine.

2. The transdermal delivery device of claim 1, wherein said release liner comprises a base film selected from the group consisting of polyethylene terephthalate, polypropylene, polyesters, and polyethylene.

3. The transdermal delivery device of claim 2, wherein said base film is from about 0.5 mil to about 5 mil thick.

4. The transdermal delivery device of claim 1, wherein said UV-cured silicone coating ranges from about 2000 angstroms to about 10,000 angstroms thick.

5. The transdermal delivery device of claim 1, wherein said device further comprises a second adhesive layer.

6. The transdermal delivery device of claim 5, wherein said second adhesive layer is a drug reservoir adhesive layer adjacent to said backing layer and to said adhesive layer, wherein said adhesive layer is a skin contact adhesive layer.

7. The transdermal delivery device of claim 6, wherein an amount of active pharmaceutical ingredient in said drug reservoir adhesive layer ranges from about 1% to about 30% by weight of said drug reservoir adhesive layer.

8. The transdermal delivery device of claim 6, further comprising a membrane or non-woven layer between said drug reservoir adhesive layer and said skin contact adhesive layer.

9. A transdermal delivery device comprising a backing layer, an adhesive layer, and a release liner coated with UV-cured silicone, wherein said UV-cured silicone coating ranges from about 2000 angstroms to about 10,000 angstroms thick, wherein said adhesive layer comprises 39 weight percent (wt %) of a mineral oil, 48 wt % of polyisobutylene (PIB), 5 wt % of colloidal silicon dioxide (CSD), and 8 wt % of an active pharmaceutical ingredient, wherein said PIB of said adhesive layer is in contact with the release liner, wherein said active pharmaceutical ingredient is clonidine, and wherein a release force necessary to remove said coated release liner ranges from about 12 grams per inch to about 19 grams per inch.

10. The transdermal delivery device of claim 1, wherein a peel force between the release liner and the adhesive layer ranges from 12 to 19 grams per inch (g/in).

* * * * *